United States Patent [19]

Shibata et al.

[11] Patent Number: 4,582,858
[45] Date of Patent: Apr. 15, 1986

[54] PROCESS FOR THE PRODUCTION OF MIXED ALCOHOLS

[75] Inventors: Masatoshi Shibata; Yoshinobu Aoki; Tsutomu Uchiyama, all of Sodegaura, Japan

[73] Assignee: Research Association for Petroleum Alternatives Development, Tokyo, Japan

[21] Appl. No.: 742,634

[22] Filed: Jun. 7, 1985

Related U.S. Application Data

[63] Continuation of Ser. No. 551,325, Nov. 14, 1983, abandoned.

[30] Foreign Application Priority Data

Nov. 29, 1982 [JP] Japan .................. 57-207662

[51] Int. Cl.$^4$ ............................ C07C 27/06
[52] U.S. Cl. .................................. 518/713
[58] Field of Search ......................... 518/713

[56] References Cited

U.S. PATENT DOCUMENTS 1,963,119  6/1934  Dreyfus ................ 518/714
4,440,668  4/1984  Chang et al. .......... 518/713

Primary Examiner—Howard T. Mars
Attorney, Agent, or Firm—Frishauf, Holtz, Goodman & Woodward

[57] ABSTRACT

A process for producing a mixed alcohol by contacting a synthesis gas with a catalyst, wherein the catalyst is a solid substance prepared by:

calcining a mixture of (A) a copper compound, (B) a nickel compound, and (C) a compound of at least one metal selected from the metals belonging to Groups II–VII of the Periodic Table;

impregnating the above-calcined product with (D) an alkali metal compound and/or an alkaline earth metal compound;

calcining the resulting mixture; and reducing the thus-calcined product.

The selectivity of the mixed alcohol is high in the process of the present invention. This is one of the advantages of the present invention. Furthermore the proportion of alcohols other than methanol in the mixed alcohol is relatively high, and thus the mixed alcohol is suitable for use as an alcohol component to be compounded to gasoline.

8 Claims, No Drawings

PROCESS FOR THE PRODUCTION OF MIXED ALCOHOLS

This application is a continuation, of application Ser. No. 551,325, filed Nov. 14, 1983, now abandoned.

BACKGROUND OF THE INVENTION

In view of a rise in price of gasoline for cars due to the aggravation of oil situation, an attempt to produce inexpensive car fuel by adding mixed alcohols to gasoline have been made in recent years. The reason why mixed alcohols are used as an alcohol component to be added to gasoline is that if methanol alone is added to gasoline, it combines together with water in gasoline to form a water/methanol mixture, resulting in the formation of two layers, i.e., a gasoline layer and a water/methanol mixed layer, in a storage tank.

Various methods of producing such mixed alcohols have been proposed. Japanese Patent Application Laid-Open No. 7727/1981, for example, discloses a process for producing mixed alcohols from synthesis gas by the use of a rhodiumbase catalyst. This process, however, is not preferred in that large amounts of by-products such as acetic acid and aldehyde result. In addition, as catalysts for use in the production of mixed alcohols from synthesis gas, a rutheniumbase catalyst (Japanese Patent Application Laid-Open No. 82327/1982), alkali metal-modified ones of a zinc-chromium catalyst and a copper-zinc catalyst (Japanese Patent Application Laid-Open No. 10689/1982), and a copper-cobalt catalyst (Japanese Patent Application Laid-Open No. 85530/1980) are known. Methods utilizing these catalysts, however, should be performed under elevated pressures. This will need expensive equipment and cause many side reactions. Hence they cannot be said to be advantageous for practical use.

SUMMARY OF THE INVENTION

The present invention is intended to overcome the above-described problems of conventional methods, and an object of the invention is to provide a process for producing mixed alcohols from synthesis gas with efficiency under relatively low pressures.

The present invention relates to a process for producing a mixed alcohol comprising methanol and higher alcohols than methanol by contacting synthesis gas with a catalyst, wherein the catalyst is a solid substance prepared by:

calcining a mixture of (A) a copper compound, (B) a nickel compound, and (C) a compound of at least one metal selected from the metals belonging to Groups II, III and IV and the fourth period of Groups V, VI and VII of the Periodic Table:

impregnating the above-calcined product with (D) an alkali metal compound and/or an alkaline earth metal compound;

calcining the resulting mixture; and reducing the thus-calcined product.

DETAILED DESCRIPTION OF THE INVENTION

A method of preparing the catalyst of the invention will hereinafter be explained in detail.

As Compound (A), any suitable compound containing copper can be used. Usually water-soluble compounds are preferred. Suitable examples of copper compounds include copper nitrate, copper sulfate, and copper chloride.

Compound (B), any suitable compound containing nickel. Particularly preferred are water-soluble compounds. Suitable examples of nickel compounds include nickel nitrate, nickel sulfate, and nickel chloride.

Compound (C) is a compound of at least one metal selected from the metals belonging to Groups II, III and IV, and the fourth period of Groups V, VI and VII of the Periodic Table. Typical examples of the metals belonging to Groups II, III and IV of the Periodic Table are magnesium, calcium, zinc, boron, aluminum, gallium, lanthanum, silicon, germanium, titanium, tin, and zirconium. Suitable examples of the metals belonging to the fourth period of Groups V, VI and VII of the Periodic Table are vanadium, chromium, and manganese. As Compound (C), various compounds of the metals as described above, such as the nitrates, sulfates, chlorides, and oxides thereof, can be used. Particularly preferred are water-soluble compounds.

As Compound (C), a salt of titanium is one of the preferable compounds. Especially titanium sulfate is preferable. Other salts such as titanium tetrachloride are undesirable here. When dissolved into water, titanium tetrachloride, for instance, is difficult to treat since it fumes and is hydrolyzed not to be dispersed homogeneously. Moreover, other salts are insoluble in water.

Titanium sulfate is a favourable salt for dispersing of titanium into catalyst as is described above, but sulfate radicals tend to remain in catalyst. When sulfur portion is 0.5% by weight or more, catalytic activity is scarcely observed.

Accordingly, when titanium sulfate is employed for producing catalyst, it is inevitable to remove sulfate radicals to make sulfur portion less than 0.5% by weight after precipitate results.

After earnest researches in removal of sulfate radicals, we have found that following two processes are desirable.

One of the processes is to repeat washing with aqueous solution of sodium chloride after the precipitate results, and to exchange sulfate radicals with chlorine ions to reduce sulfate radicals, and thus make sulfur portion less than 0.5% by weight. Thereupon, the concentration of the aqueous solution of sodium chloride is desired to be 0.1 mole per liter - 5 mole per liter.

Another process is to adjust pH at co-precipitating by addition of sodium carbonate. There, once co-precipitation is made at pH 9.0 or more, after that the washing with plain water can reduce the sulfate radicals to make the sulfur portion less than 0.5% by weight. When pH is less than 9.0, activity does not arise sufficiently.

In the preparation of the catalyst of the invention, Compounds (A), (B) and (C) are first mixed and calcined.

Compounds (A), (B) and (C) can be mixed by techniques such as a co-precipitation method, a kneading method, and a dipping method. In accordance with the co-precipitation method, for example, they are added to water to form aqueous solutions or suspensions, which are then mixed and co-precipitated by adjusting the pH through addition of a co-precipitating agent such as sodium carbonate, sodium hydroxide, and potassium hydroxide at room temperature or at elevated temperatures. Then, the resulting precipitate is aged, if necessary, and washed with water, dried and calcined at a temperature of from 200° to 500° C.

The above-calcinated product is then impregnated with Compound (D), i.e., an alkali metal compound and/or an alkaline earth metal compound. Compound (D) is preferably water-soluble. Suitable examples include sodium carbonate and magnesium acetate. In the impregnation of the calcined product, Compound (D) is used as an aqueous solution; that is, the calcined product is impregnated with an aqueous solution of Compound (D). After the process of impregnation, the resulting mixture should be calcined again. This calcination is usually performed at a temperature of from 100° to 400° C.

Although the composition of the thus-calcined product varies with the amounts of Compounds (A), (B), (C) and (D) being added, it is necessary for the molar ratio of (A) to (B) to (C) to (D) (calculated as oxide) to be controlled so that $0.05 < (A) < 0.7$, $0.01 < (B) < 0.7$, $0.01 < (C) < 0.7$, and $0.005 < (D) < 0.3$.

The calcined product is then reduced. This reduction is sufficient to be performed at a temperature of from 200° to 400° C. by the use of a reducing atmosphere, for example, in the presence of hydrogen or carbon monoxide.

The thus-prepared solid substance is used as the catalyst of the invention.

Although Compounds (A), (B), (C) and (D) can be mixed and calcined simultaneously, Compound (D) of alkali or alkaline earth metal compound is dispersed only insufficiently and unevenly in the final product by such a procedure. Hence this procedure fails to produce the desired catalyst.

In the process of the invention, the solid substance as prepared above is used as a catalyst, and synthesis gas, i.e., a mixed gas of hydrogen and carbon monoxide, is contacted with the catalyst to produce a mixed alcohol. The composition of the synthesis gas to be used as a feed in the process of the invention is not critical. In general, however, it is preferred to use synthesis gas in which the molar ratio of hydrogen to carbon monoxide is within the range of from 1:3 to 3:1.

Other reaction conditions for the process of the invention are not critical and can be determined appropriately. The reaction temperature is usually from 200° to 500° C. and preferably from 240° to 400° C.; the reaction pressure may be relatively low, in general, ranges between 20 and 200 kilograms per square centimeter (by gauge) and preferably between 40 and 100 kilograms per square centimeter (by gauge); and the gas hourly space velocity (GHSV) is from 500 to 100,000 per hour and preferably from 1,000 to 50,000 per hour.

The process of the invention as described above produces mixed alcohols comprising methanol and higher alcohols than methanol, such as ethanol, propanol, and butanol, and other compounds such as aldehydes and esters. The selectivity of the mixed alcohol is high in the process of the invention. This is one of the advantages of the present invention. Another advantage is that the costs of equipment and operation, for example, can be greatly reduced, since the reaction pressure in the process of the invention is sufficient to be relatively low. Furthermore the proportion of alcohols other than methanol in the mixed alcohol as produced by the process of the invention is relatively high, and thus the mixed alcohol is suitable for use as an alcohol component to be compounded to gasoline.

The present invention is described in greater detail with reference to the following examples.

EXAMPLE 1

An aqueous solution (Aqueous Solution I) (2.5 liters) containing 48.3 grams of copper nitrate (3 hydrate), 29.1 grams of nickel nitrate (6 hydrate), and 59.5 grams of zinc nitrate (6 hydrate) was prepared and heated to 60° C. Separately 2.5 liters of an aqueous solution (Aqueous Solution II) containing 81.3 grams of sodium carbonate (anhydrous) was prepared and heated to 60° C.

These aqueous solutions were mixed rapidly and, after completion of precipitation, aged. Then the resulting mixture was filtered, and the precipitate thus obtained was washed sufficiently with water, dried at 120° C. for about 12 hours and then calcined at 450° C. for 2 hours.

The thus-calcined product was impregnated with an aqueous solution (Aqueous Solution III) containing 6.8 grams of sodium carbonate (anhydrous) and dried at 120° C. for about 12 hours. Then graphite was added, and the resulting mixture was pelletized and pulverized to produce 16-32 mesh grains. The thus-prepared catalyst precursor had a composition of Cu:Ni:Zn:Na=0.36:0.18:0.36:0.10 (molar ratio).

Then 1 milliliter of the catalyst precursor was packed in a reaction tube of stainless steel. While passing a 1:9 (molar ratio) mixture of carbon monoxide and nitrogen as a reducing gas through the reaction tube at a gas hourly space velocity (GHSV) of 4,000 per hour, the catalyst precursor was gradually heated and reduced at 240° C. for 5-20 hours to produce a catalyst.

A synthesis gas (carbon monoxide:hydrogen=1:2 (molar ratio)) was introduced into the reaction tube at a gas hourly space velocity (GHSV) of 4,000 per hour. The pressure was gradually increased to 50 kilograms per square centimeter (by gauge). Then the temperature was increased to a reaction temperature at which the conversion of carbon monoxide (excluding the one converted into carbon dioxide) reached about 20%. The reaction products were passed through a tube maintained at 200° C., without being condensed at the outlet of the reaction tube, and introduced into a gas chromatography instrument where they were analyzed. The column filler as used in this gas chromatography analysis was a mixture of activated carbon, Porapak-Q (produced by Water Co.) and Porapak-R (produced by Water Co.). The results are shown in Table 1.

EXAMPLE 2

A catalyst precursor was prepared in the same manner as in Example 1 except that 2.5 liters of an aqueous solution containing 48.3 grams of copper nitrate (3 hydrate), 29.1 grams of nickel nitrate (6 hydrate), and 75.0 grams of aluminum nitrate (9 hydrate) was used as Aqueous Solution I and 2.5 liters of an aqueous solution containing 90.2 grams of sodium carbonate (anhydrous) as Aqueous Solution II. This catalyst precursor had a composition of Cu:Ni:Al:Na=0.36:0.18:0.36:0.10 (molar ratio).

The catalyst precursor was reduced in the same manner as in Example 1 to form a catalyst. Using the thus-prepared catalyst, the production of mixed alcohol from synthesis gas was performed in the same manner as in Example 1. The results are shown in Table 1.

EXAMPLE 3

A catalyst precursor was prepared in the same manner as in Example 1 except that 2.5 liters of an aqueous solution containing 48.3 grams of copper nitrate (3 hydrate), 29.1 grams of nickel nitrate (6 hydrate), and 75.0 grams of aluminum nitrate (9 hydrate) was used as Aqueous Solution I, 2.5 liters of an aqueous solution containing 90.2 grams of sodium carbonate (anhydrous) as Aqueous Solution II, and an aqueous solution containing 13.7 grams of magnesium acetate (4 hydrate) as Aqueous Solution III for the process of impregnation. This catalyst precursor had a composition of Cu:Ni:Al:Mg=0.36:0.18:0.36:0.10 (malar ratio).

The catalyst precursor was reduced in the same manner as in Example 1 to form a catalyst. Using the thus-prepared catalyst, the production of mixed alcohol from synthesis gas was performed in the same manner as in Example 1. The results are shown in Table 1.

EXAMPLE 4

A catalyst precursor was prepared in the same manner as in Example 1 except that 2.5 liters of an aqueous solution containing 48.3 grams of copper nitrate (3 hydrate), 29.1 grams of nickel nitrate (6 hydrate), and 79.9 grams of gallium nitrate (8 hydrate) was used as Aqueous Solution I, and 2.5 liters of an aqueous solution containing 91.6 grams of sodium carbonate (anhydrous) as Aqueous Solution II. This catalyst precursor had a composition of Cu:Ni:Ga:Na=0.36:0.18:0.36:0.10 (molar ratio).

The catalyst precursor was reduced in the same manner as in Example 1 to form a catalyst. Using the thus-prepared catalyst, the production of mixed alcohol from synthesis gas was performed in the same manner as in Example 1. The results are shown in Table 1.

EXAMPLE 5

A catalyst precursor was prepared in the same manner as in Example 1 except that 2.5 liters of an aqueous solution containing 48.3 grams of copper nitrate (3 hydrate) and 29.1 grams of nickel nitrate (6 hydrate) was used as Aqueous Solution I, and 2.5 liters of an aqueous solution containing 61.7 grams of water glass ($SiO_2$ content: 28.6% by weight) and 37.2 grams of sodium carbonate (anhydrous) as Aqueous Solution II. This catalyst precursor had a composition of Cu:Ni:Si:Na=0.36:0.18:0.36:0.10 (molar ratio).

The catalyst precursor was reduced in the same manner as in Example 1 to form a catalyst. Using the thus-prepared catalyst, the production of mixed alcohol from synthesis gas was performed in the same manner as in Example 1. The results are shown in Table 1.

EXAMPLE 6

A catalyst precursor was prepared in the same manner as in Example 1 except that 2.5 liters of an aqueous solution containing 48.3 grams of copper nitrate (3 hydrate), 29.1 grams of nickel nitrate (6 hydrate), and 64.4 grams of zirconium oxychloride (8 hydrate) was used as Aqueous Solution I, and 2.5 liters of an aqueous solution containing 63.7 grams of sodium carbonate (anhydrous) as Aqueous Solution II. This catalyst precursor had a composition of Cu:Ni:Zr:Na=0.36:0.18:0.36:0.10 (molar ratio).

The catalyst precursor was reduced in the same manner as in Example 1 to form a catalyst. Using the thus-prepared catalyst, the production of mixed alcohol from synthesis gas was performed in the same manner as in Example 1. The results are shown in Table 1.

EXAMPLE 7

An aqueous solution (2.5 liters) containing 48.3 grams of copper nitrate (3 hydrate), 29.1 grams of nickel nitrate (6 hydrate), and 161.1 grams of titanium sulfate ($Ti(SO_4)_2$ content: 29.8% by weight) was prepared and heated to 60° C. Separately 2.5 liters of an aqueous solution containing 128.0 grams of sodium carbonate (anhydrous) was prepared and heated to 60° C. These aqueous solutions were mixed rapidly and, after completion of precipitation, aged. The resulting mixture was filtered, and the precipitate thus obtained was treated with an aqueous solution of sodium chloride (concentration: 0.5 mole per liter) and further washed sufficiently with water.

Thereafter the same procedure as in Example 1 was performed to form a catalyst precursor. This catalyst precursor had a composition of Cu:Ni:Ti:Na=0.36:0.18:0.36:0.10 (molar ratio).

The catalyst precursor was reduced in the same manner as in Example 1 to form a catalyst. Using the thus-prepared catalyst, the production of mixed alcohol from synthesis gas was performed in the same manner as in Example 1. The results are shown in Table 1.

EXAMPLE 8

A catalyst precursor was prepared in the same manner as in Example 1 except that 2.5 liters of an aqueous solution containing 48.3 grams of copper nitrate (3 hydrate), 29.1 grams of nickel nitrate (6 hydrate), and 80.0 grams of chromium nitrate was used as Aqueous Solution I, and 2.5 liters of an aqueous solution containing 90.8 grams of sodium carbonate (anhydrous) as Aqueous Solution II. This catalyst precursor had a composition of Cu:Ni:Cr:Na=0.38:0.19:0.31:0.12 (molar ratio).

The catalyst precursor was reduced in the same manner as in Example 1 to form a catalyst. Using the thus-prepared catalyst, the production of mixed alcohol from synthesis gas was performed in the same manner as in Example 1. The results are shown in Table 1.

EXAMPLE 9

A catalyst precursor was prepared in the same manner as in Example 1 except that 2.5 liters of an aqueous solution containing 48.3 grams of copper nitrate (3 hydrate), 29.1 grams of nickel nitrate (6 hydrate), and 86.6 grams of lanthanum nitrate (6 hydrate) was used as Aqueous Solution I, and 2.5 liters of an aqueous solution containing 74.2 grams of sodium carbonate (anhydrous) as Aqueous Solution II. This catalyst precursor had a composition of Cu:Ni:La:Na=0.36:0.18:0.36:0.10 (molar ratio).

The catalyst precursor was reduced in the same manner as in Example 1 to form a catalyst. Using the thus-prepared catalyst, the production of mixed alcohol from synthesis gas was performed in the same manner as in Example 1. The results are shown in Table 1.

EXAMPLE 10

A catalyst precursor was prepared in the same manner as in Example 1 except that 2.5 liters of an aqueous solution containing 48.3 grams of copper nitrate (3 hydrate), 29.1 grams of nickel nitrate (6 hydrate), and 86.6 grams of lanthanum nitrate (6 hydrate) was used as Aqueous Solution I, 2.5 liters of an aqueous solution containing 74.2 grams of sodium carbonate (anhydrous) as Aqueous Solution II, and an aqueous solution containing 13.7 grams of magnesium acetate (4 hydrate) as Aqueous Solution III for the process of impregnation. This catalyst precursor had a composition of Cu:Ni:La:Mg=0.36:0.18:0.36:0.10 (molar ratio).

The catalyst precursor was reduced in the same manner as in Example 1 to form a catalyst. Using the thus-prepared catalyst, the production of mixed alcohol from synthesis gas was performed in the same manner as in Example 1. The results are shown in Table 1.

EXAMPLE 11

A catalyst precursor was prepared in the same manner as in Example 1 except that 2.5 liters of an aqueous solution containing 48.3 grams of copper nitrate (3 hydrate), 29.1 grams of nickel nitrate (6 hydrate), and 25.6 grams of magnesium nitrate (6 hydrate) was used as Aqueous Solution I, and 2.5 liters of an aqueous solution containing 50.3 grams of sodium carbonate (anhydrous) as Aqueous Solution II. This catalyst precursor had a composition of Cu:Ni:Mg:Na=0.43:0.22:0.22:0.13 (molar ratio).

The catalyst precursor was reduced in the same manner as in Example 1 to form a catalyst. Using the thus-prepared catalyst, the production of mixed alcohol from synthesis gas was performed in the same manner as in Example 1. The results are shown in Table 1.

pared catalyst precursor had a composition of Cu:Ni:Ti:Na=1:1:1:0.38 (molar ratio).

The catalyst precursor was reduced in the same manner as in Example 1 to form a catalyst. Using the thus-prepared catalyst, the production of mixed alcohol from synthesis gas was performed in the same manner as in Example 1. The results are shown in Table 2.

EXAMPLE 13

A catalyst precursor was prepared in the same manner as in Example 12 except that 1.5 liters of an aqueous solution containing 16.1 grams of copper nitrate (3 hydrate), 29.1 grams of nickel nitrate (6 hydrate), and 106.7 grams of titanium sulfate (the same as used in Example 12) was used as Aqueous Solution I, and 1.5 liters of an aqueous solution containing 79.5 grams of sodium carbonate (anhydrous) as Aqueous Solution II. This catalyst precursor had a composition of Cu:Ni:Ti:Na=2:3:4:1.15 (molar ratio).

The catalyst precursor was reduced in the same manner as in Example 12 to form a catalyst. Using the thus-prepared catalyst, the production of mixed alcohol from synthesis gas was performed in the same manner as in Example 12. The results are shown in Table 2.

TABLE 1

| Example | Reaction Temperature (°C.) | Conversion of Carbon Monoxide*1 (%) | Selectivity of Alcohol*2 (%) | Composition of Mixed Alcohol (% by weight) | | | |
|---|---|---|---|---|---|---|---|
| | | | | Methanol | Ethanol | Propanol | Butanol and Higher Alcohols than Butanol |
| 1 | 311 | 20 | 70 | 88 | 8 | 3 | 1 |
| 2 | 305 | 22 | 55 | 55 | 29 | 8 | 8 |
| 3 | 315 | 21 | 68 | 89 | 8 | 2 | 1 |
| 4 | 307 | 19 | 53 | 58 | 27 | 8 | 7 |
| 5 | 312 | 21 | 52 | 53 | 28 | 11 | 8 |
| 6 | 333 | 21 | 43 | 82 | 10 | 4 | 4 |
| 7 | 307 | 19 | 46 | 45 | 37 | 10 | 8 |
| 8 | 335 | 20 | 69 | 87 | 9 | 3 | 1 |
| 9 | 331 | 20 | 55 | 77 | 15 | 1 | 1 |
| 10 | 334 | 19 | 52 | 78 | 14 | 6 | 2 |
| 11 | 319 | 21 | 47 | 57 | 30 | 8 | 5 |

Note $$*^1\text{Conversion of Carbon Monoxide} = \frac{\text{Amount of Carbon Monoxide Converted into Alcohol (moles)} - \text{Amount of Carbon Dioxide Formed (moles)}}{\text{Amount of Carbon Monoxide Introduced (moles)}} \times 100$$

$$*^2\text{Selectivity of Alcohol} = \frac{\text{Amount of Carbon Monoxide Converted into Alcohol (moles)}}{\text{Amount of Carbon Monoxide Converted (moles)} - \text{Amount of Carbon Dioxide Formed (moles)}} \times 100$$

EXAMPLE 12

An aqueous solution (Aqueous Solution I)(1.5 liters) containing 24.2 grams of copper nitrate (3 hydrate), 29.1 grams of nickel nitrate (6 hydrate), and 80 grams of titanium sulfate (Ti(SO$_4$)$_2$ content: 29.8% by weight) was prepared and heated to 60° C. Separately 1.5 liters of an aqueous solution (Aqueous Solution II) containing 66.3 grams of sodium carbonate (anhydrous) was prepared and heated to 60° C. These aqueous solutions were mixed rapidly and, after completion of precipitation, aged. The resulting mixture was filtered, and the thus-obtained precipitate was treated with an aqueous sodium chloride solution (concentration: 0.5 mole per liter) and washed sufficiently with water.

The precipitate was dried at 120° C. for about 12 hours and then calcined at 450° C. for 2 hours.

The thus-calcined product was impregnated with 38 milliliters of an aqueous solution (Aqueous Solution III) of sodium carbonate (concentration: 1.0 mole per liter), and dried at 120° C. for about 12 hours. Then graphite was added, and the resulting mixture was pelletized and pulverized to form 16–32 mesh grains. The thus-pre-

EXAMPLE 14

A catalyst precursor was prepared in the same manner as in Example 1 except that 1.5 liters of an aqueous solution containing 24.1 grams of copper nitrate (3 hydrate), 29.1 grams of nickel nitrate (6 hydrate), and 28.7 grams of manganese nitrate (6 hydrate) was used as Aqueous Solution I, 1.5 liters of an aqueous solution containing 39.8 grams of sodium carbonate (anhydrous) as Aqueous Solution II, and 38 milliliters of a solution of sodium carbonate (concentration: 1.0 mole per liter) as Aqueous Solution III. This catalyst precursor had a composition of Cu:Ni:Mn:Na=1:1:1:0.38 (molar ratio).

The catalyst precursor was reduced in the same manner as in Example 12 to form a catalyst. Using the thus-prepared catalyst, the production of mixed alcohol from synthesis gas was performed in the same manner as in Example 12. The results are shown in Table 2.

EXAMPLE 15

A catalyst precursor was prepared in the same manner as in Example 1 except that 1.5 liters of an aqueous solution containing 14.5 grams of copper nitrate (3 hydrate), 8.7 grams of nickel nitrate (6 hydrate), and 60.3 grams of manganese nitrate (6 hydrate) was used as Aqueous Solution I, 1.5 liters of an aqueous solution containing 39.8 grams of sodium carbonate (anhydrous) as Aqueous Solution II, and 38 milliliters of a solution of sodium carbonate (concentration: 1.0 mole per liter) as Aqueous Solution III. This catalyst precursor had a composition of Cu:Ni:Mn:Na=2:1:7:1.28 (molar ratio).

The catalyst precursor was reduced in the same manner as in Example 12 to form a catalyst. Using the thus-prepared catalyst, the production of mixed alcohol from synthesis gas was performed in the same manner as in Example 12. The results are shown in Table 2.

EXAMPLE 16

A catalyst precursor was prepared in the same manner as in Example 1 except that 1.5 liters of an aqueous solution containing 50.7 grams of copper nitrate (3 hydrate), 8.7 grams of nickel nitrate (6 hydrate), and 17.2 grams of manganese nitrate (6 hydrate) was used as Aqueous Solution I, 1.5 liters of an aqueous solution containing 39.8 grams of sodium carbonate (anhydrous) as Aqueous Solution II, and 38 milliliters of a solution of sodium carbonate (concentration: 1.0 mole per liter) as Aqueous Solution III. This catalyst precursor had a composition of Cu:Ni:Mn:Na=7:1:2:1.28 (molar ratio).

The catalyst precursor was reduced in the same manner as in Example 12 to form a catalyst. Using the thus-prepared catalyst, the production of mixed alcohol from synthesis gas was performed in the same manner as in Example 12. The results are shown in Table 2.

in the water bath heated at 90° C. and evaporated to dryness.

The thus-obtained product was dried at 120° C. for about 5 hours. Then graphite of 2% by weight based on the product was added thereto, and the resulting mixture was pelletized (catalyst precursor). Sulfur content in the thus prepared catalyst precursor is 0.2% by weight.

The catalyst precursor was reduced in the same manner as in Example 1 to form a catalyst. Using the thus-prepared catalyst, the production of mixed alcohol from synthesis gas was performed in the same manner as in Example 1 except that the reaction pressure was gradually increased to 61 kilograms per square centimeter (by gauge).

The results are shown in Table 3.

EXAMPLE 18

A catalyst precursore was prepared in the same manner as in Example 17 except that 1.5 liters of an aqueous solution containing 199.0 grams of sodium carbonate (anhydrous) was used as Aqueous Solution II and the pH of the above described solution was 9.9. Sulfur content in the thus-prepared catalyst precursor was 0.1% by weight.

The catalyst precursor was reduced in the same manner as in Example 1 to form a catalyst. Using the thus-prepared catalyst, the production of mixed alcohol from synthesis gas was performed in the same manner as in Example 1 except that the reaction pressure was gradually increased to 61 kilograms per square centimeter (by gauge).

TABLE 2

| Example | Reaction Temperature (°C.) | Conversion of Carbon Monoxide*1 (%) | Selectivity of Alcohol*2 (%) | Composition of Mixed Alcohol (% by weight) | | | |
|---|---|---|---|---|---|---|---|
| | | | | Methanol | Ethanol | Propanol | Butanol and Higher Alcohols than Butanol |
| 12 | 318 | 21 | 51 | 31 | 41 | 13 | 15 |
| 13 | 308 | 20 | 50 | 33 | 39 | 12 | 16 |
| 14 | 251 | 19 | 62 | 43 | 49 | 6 | 2 |
| 15 | 284 | 20 | 80 | 56 | 33 | 1 | 10 |
| 16 | 256 | 20 | 64 | 45 | 48 | 2 | 5 |

Note
*1, *2 Same as in Table 1

EXAMPLE 17

One and half liters of an aqueous solution (Aqueous Solution I) containing 24.2 grams of copper nitrate (3 hydrate), 29.1 grams of nickel nitrate (6 hydrate), and 80 grams of titanium sulfate solution (Ti(SO$_4$)$_2$ content: 30% by weight) was prepared and heated to 60° C. Separately 1.5 liters of an aqueous solution (Aqueous Solution II) containing 66.3 grams of sodium carbonate (anhydrous) was prepared and heated to 90° C. These aqueous solutions I and II were mixed rapidly and maintained at 85° C. for about 2 hours with stirring vigorously to be precipitated. The pH of the above described solution was 9.2. Then the solution containing the precipitate was filtered, and the thus obtained precipitate was washed with water in 200 fold amount of the precipitate.

The precipitate was dried at 120° C. for about 10 hours and then was calcined at 450° C. for 2 hours. The thus calcined product was cooled to a room temperature, and then the product was impregnated with 19.2 milliliters of an aqueous solution (Aqueous Solution III) of sodium carbonate (concentration: 1.0 mole per liter)

The results are shown in Table 3.

EXAMPLE 19

One and half liters of an aqueous solution (Aqueous Solution I) containing 24.2 grams of copper nitrate (3 hydrate), 29.1 grams of nickel nitrate (6 hydrate), and 80 grams of titanium sulfate solution (Ti(SO$_4$)$_2$ content: 30% by weight) was prepared and heated to 60° C. Separately 1.5 liters of an aqueous solution (Aqueous Solution II) containing 66.3 grams of sodium carbonate (anhydrous) was prepared and heated to 90° C. These aqueous solutions I and II were mixed rapidly and maintained at 85° C. for about 2 hours with stirring vigourously to be precipitated. The pH of the above described solution was 9.3. Then the solution containing the precipitate was filtered, and thus obtained the precipitate was washed with water in 200 fold amount of the precipitate.

The precipitate was sufficiently suspended in 2 liters of an aqueous solution (80° C.) of sodium chrolide (concentration: 0.5 mole per liter), and was separated by filtration. Then the precipitate was washed again with water in 200 fold amount of the precipitate.

The precipitate was dried at 120° C. for about 10 hours and then calcined at 450° C. for 2 hours. The thus-calcined product was cooled to a room temperature, and then the product was impregnated with 19.2 milliliters of an aqueous solution (Aqueous Solution III) of sodiumcarbonate (concentration: 1.0 mole per liter) in the water bath heated at 90° C. and evaporated to dryness.

The thus-obtained product was dried at 120° C. for about 5 hours. Then graphite of 2% by weight based on the product was added thereto, and the resulting mixture was pelletized (catalyst precursor). Sulfur content in the thus-prepared catalyst precursor is 0.2% by weight.

The catalyst precursor was reduced in the same manner as in Example 1 to form a catalyst. Using the thus-prepared catalyst, the production of mixed alcohol from synthesis gas was performed in the same manner as in Example 1 except that the reaction pressure was gradually increased to 61 kilograms per square centimeter (by gauge).

The results are shown in Table 3.

EXAMPLE 20

A catalyst precursor was prepared in the same manner as in Example 19 except that 1.5 liters of an aqueous solution containing 53.0 grams of sodium carbonate (anhydrous) was used as Aqueous Solution II and the pH of the above solution was 8.0. Sulfur content in the thus-prepared catalyst precursor was 0.5% by weight.

The catalyst precursor was reduced in the same manner as in Example 1 to form a catalyst. Using the thus-prepared catalyst, the production of mixed alcohol from synthesis gas was performed in the same manner as in Example 1 except that the reaction pressure was gradually increased to 61 kilograms per square centimeter (by gauge).

The results are shown in Table 3.

the improvement comprising using as said catalyst, a solid catalyst prepared by calcining a mixture of (A) a copper compound, (B) a nickel compound, and (C) a compound of at least one metal selected from the group consisting of aluminum, manganese, titanium, gallium and silicon to form a calcined product;

impregnating said calcined product with (D) an alkali metal compound;

wherein the molar ratio of (A) to (B) to (C) to (D), calculated as the oxide, is controlled so that $0.05 < (A) < 0.7, 0.01 < (B) < 0.7, 0.01 < (C) < 0.7$, and $0.005 < (D) < 0.3$;

heating said calcined product impregnated with said alkali metal compound to form an alkali metal-containing calcined product; and reducing said alkali metal-containing calcined product to form said catalyst.

2. The process for the production of mixed alcohols as claimed in claim 1, wherein the Compound (D) is a sodium compound.

3. The process for the production of mixed alcohols as claimed in claim 1, wherein the Compound (C) is an aluminum compound and the Compound (D) is a sodium compound.

4. The process for the production of mixed alcohols as claimed in claim 1, wherein the Compound (C) is an aluminum compound.

5. The process for the production of mixed alcohols as claimed in claim 1, wherein the Compound (C) is a gallium compound and the Compound (D) is sodium compound.

6. The process for the production of mixed alcohols as claimed in claim 1, wherein the Compound (C) is a silicon compound and the Compound (D) is sodium compound.

7. The process for the production of mixed alcohols as claimed in claim 1, wherein the Compound (C) is a

TABLE 3

| Example | Reaction Temperature (°C.) | Conversion of Carbon Monoxide*1 (%) | Selectivity of Oxygen-containing Compounds*2 (%) | Composition of Oxygen-containing compounds formed (% by weight) | | | | | | | |
|---|---|---|---|---|---|---|---|---|---|---|---|
| | | | | Methanol | Ethanol | Propanol | Butanol and Higher Alcohols than Butanol | Dimethyl ether | Acetaldehyde | Acetone | Methyl ethyl ketone |
| 17 | 297 | 19 | 58 | 56 | 31 | 4 | 4 | <1 | 2 | 2 | <1 |
| 18 | 297 | 19 | 65 | 57 | 23 | 11 | 6 | <1 | 1 | 2 | <1 |
| 19 | 307 | 20 | 54 | 55 | 33 | 5 | 4 | 0 | 1 | 2 | <1 |
| 20 | 307 | 19 | 53 | 59 | 24 | 12 | 3 | 0 | 0 | 2 | 0 |

Note:

*1 Conversion of Carbon Monoxide = $\dfrac{\text{Amount of Carbon Monoxide Converted into Alcohol (moles)} - \text{Amount of Carbon Dioxide Formed (moles)}}{\text{Amount of Carbon Monoxide Introduced (moles)}} \times 100$

*2 Selectivity of Oxygen-containing Compounds = $\dfrac{\text{Amount of Carbon Monoxide Converted into Oxygen-containing Compounds (moles)}}{\text{Amount of Carbon Monoxide Converted (moles)} - \text{Amount of Carbon Dioxide Formed (moles)}} \times 100$

What is claimed is:

1. In a process for producing a mixed alcohol comprising methanol and higher alcohols than methanol comprising contacting a synthesis gas with a catalyst whereby methanol and higher alcohols are formed and recovered, titanium compound and the Compound (D) is sodium compound.

8. The process for the production of mixed alcohols as claimed in claim 1, wherein the Compound (C) is a manganese compound and the Compound (D) is a sodium compound.

* * * * *